United States Patent
Eubanks et al.

(10) Patent No.: US 10,632,245 B2
(45) Date of Patent: *Apr. 28, 2020

(54) INTERVENTIONAL CATHETER ASSEMBLIES, CONTROL CONSOLES AND ADAPTIVE TUBING CASSETTES

(71) Applicant: BOSTON SCIENTIFIC LIMITED, Hamilton (BM)

(72) Inventors: Shannon Eubanks, Woodinville, WA (US); Keith Schubert, Redmond, WA (US); Peter Bristol, Shoreline, WA (US); Patrick Vilbrandt, Edmonds, WA (US)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 169 days.

This patent is subject to a terminal disclaimer.

(21) Appl. No.: 15/723,586

(22) Filed: Oct. 3, 2017

(65) Prior Publication Data
US 2018/0036474 A1 Feb. 8, 2018

Related U.S. Application Data

(60) Continuation of application No. 13/743,173, filed on Jan. 16, 2013, now Pat. No. 9,775,964, which is a
(Continued)

(51) Int. Cl.
*A61M 3/02* (2006.01)
*A61B 17/3207* (2006.01)
(Continued)

(52) U.S. Cl.
CPC ........ *A61M 3/0283* (2013.01); *A61B 17/3207* (2013.01); *A61B 17/320758* (2013.01);
(Continued)

(58) Field of Classification Search
CPC .............. F04B 43/1253; F04B 43/0072; F04B 43/082; F04B 43/12; F04B 43/1261;
(Continued)

(56) References Cited

U.S. PATENT DOCUMENTS 3,864,786 A 2/1975 Salice
3,952,368 A 4/1976 Zernig et al.
(Continued)

FOREIGN PATENT DOCUMENTS

EP 0319272 A2 6/1989
EP 0731275 A1 9/1996
(Continued)

OTHER PUBLICATIONS

Pathway Medical Technologies, Inc., "International Search Report and Written Opinion," International Patent Application No. PCT/US2011/044279, filed Jul. 15, 2011 (dated Dec. 8, 2011).
(Continued)

*Primary Examiner* — Bradley J Osinski
(74) *Attorney, Agent, or Firm* — Seager, Tufte & Wickhem, LLP

(57) ABSTRACT

Interventional catheter assemblies, operating systems and adaptive interface components allow operation of a variety of interventional catheter assemblies, including infusion catheters, aspiration catheters and interventional catheters that provide both infusion and aspiration, using a common control console housing infusion and aspiration systems. Adaptive tubing cassettes having a handle and one or more preformed tubing loops route aspiration and/or infusion tubing in a predetermined configuration to mate with aspiration and infusion systems on a control console.

18 Claims, 9 Drawing Sheets

Related U.S. Application Data division of application No. 12/854,834, filed on Aug. 11, 2010, now Pat. No. 8,388,582.

(60) Provisional application No. 61/233,434, filed on Aug. 12, 2009.

(51) Int. Cl.

| | | |
|---|---|---|
| *A61M 1/00* | (2006.01) | |
| *A61M 25/00* | (2006.01) | |
| *A61M 39/10* | (2006.01) | |
| *A61M 5/142* | (2006.01) | |
| *A61B 17/00* | (2006.01) | |
| *A61B 17/22* | (2006.01) | |

(52) U.S. Cl.
CPC .......... *A61M 1/0064* (2013.01); *A61M 3/022* (2014.02); *A61M 3/0208* (2014.02); *A61M 5/14232* (2013.01); *A61M 25/0021* (2013.01); *A61M 39/10* (2013.01); *A61B 2017/00199* (2013.01); *A61B 2017/00482* (2013.01); *A61B 2017/22079* (2013.01); *A61M 2205/12* (2013.01); *A61M 2205/50* (2013.01); *A61M 2209/084* (2013.01)

(58) Field of Classification Search
CPC .............. F04B 43/1292; F04B 43/1223; F04B 43/1276; F04B 43/1238; F04B 43/1215; A61M 3/0283; A61M 5/14232; A61M 39/10; A61M 25/0021; A61M 2205/12
See application file for complete search history.

(56) References Cited

U.S. PATENT DOCUMENTS

| | | | |
|---|---|---|---|
| 4,025,376 A | 5/1977 | Schirmer | |
| 4,035,093 A | 7/1977 | Redshaw | |
| 4,075,735 A | 2/1978 | Rock et al. | |
| 4,085,481 A | 4/1978 | Lautenschlager | |
| 4,155,362 A | 5/1979 | Jess | |
| 4,187,057 A | 2/1980 | Xanthopoulos | |
| 4,256,442 A | 3/1981 | Lamadrid et al. | |
| 4,500,269 A | 2/1985 | Jess | |
| 4,558,996 A | 12/1985 | Becker | |
| 4,655,197 A | 4/1987 | Atkinson | |
| 4,705,038 A | 11/1987 | Sjostrom et al. | |
| 4,798,580 A | 1/1989 | DeMeo et al. | |
| 4,813,855 A | 3/1989 | Leveen et al. | |
| 4,824,339 A | 4/1989 | Bainbridge et al. | |
| 4,861,242 A | 8/1989 | Finsterwald | |
| 4,925,376 A | 5/1990 | Kahler | |
| 4,925,444 A | 5/1990 | Orkin et al. | |
| 4,977,646 A | 12/1990 | McCraw | |
| 5,082,429 A | 1/1992 | Soderquist et al. | |
| 5,106,366 A | 4/1992 | Steppe | |
| 5,181,842 A | 1/1993 | Sunderland et al. | |
| 5,195,960 A | 3/1993 | Hossain et al. | |
| RE34,556 E | 3/1994 | Sjostrom et al. | |
| 5,380,173 A | 1/1995 | Hellstrom | |
| 5,381,510 A | 1/1995 | Ford et al. | |
| 5,433,588 A | 7/1995 | Monk et al. | |
| 5,460,490 A | 10/1995 | Carr et al. | |
| 5,468,129 A | 11/1995 | Sundén et al. | |
| 5,484,239 A | 1/1996 | Chapman et al. | |
| 5,549,458 A | 8/1996 | Chapman et al. | |
| 5,588,815 A | 12/1996 | Zaleski, II | |
| 5,769,811 A | 6/1998 | Stacey et al. | |
| 5,845,530 A | 12/1998 | Brockmeyer et al. | |
| 5,927,956 A | 7/1999 | Lim et al. | |
| 5,928,177 A | 7/1999 | Brugger et al. | |
| 6,019,582 A | 2/2000 | Green | |
| 6,059,544 A | 5/2000 | Jung et al. | |
| 6,077,246 A | 6/2000 | Kullas et al. | |
| 6,200,287 B1 * | 3/2001 | Keller ................. | A61M 1/3693 210/767 |
| 6,494,693 B1 | 12/2002 | Sundén | |
| 6,511,454 B1 | 1/2003 | Nakao et al. | |
| 6,719,717 B1 | 4/2004 | Johnson et al. | |
| 6,722,865 B2 | 4/2004 | Domroese | |
| 6,926,726 B2 | 8/2005 | Drasler et al. | |
| 6,962,488 B2 | 11/2005 | Davis et al. | |
| 7,024,717 B2 | 4/2006 | Hilscher et al. | |
| 7,169,352 B1 | 1/2007 | Felt et al. | |
| 7,214,038 B2 | 5/2007 | Saxer et al. | |
| 7,238,010 B2 | 7/2007 | Hershberger et al. | |
| 7,239,916 B2 | 7/2007 | Thompson et al. | |
| 7,273,359 B2 | 9/2007 | Blight et al. | |
| 7,478,999 B2 | 1/2009 | Limoges | |
| D600,792 S | 9/2009 | Eubanks et al. | |
| 8,393,879 B2 | 3/2013 | Kent | |
| 2005/0053502 A1 | 3/2005 | Souza | |
| 2007/0073233 A1 | 3/2007 | Thor et al. | |
| 2007/0243088 A1 | 10/2007 | North | |
| 2007/0253850 A1 | 11/2007 | Williams | |
| 2008/0154095 A1 * | 6/2008 | Stubkjaer ............ | A61M 3/0258 600/156 |
| 2008/0175734 A1 | 7/2008 | LaBanco et al. | |
| 2009/0129944 A1 | 5/2009 | Stemple et al. | |
| 2009/0192498 A1 | 7/2009 | Andrew et al. | |
| 2013/0131585 A1 | 5/2013 | Eubanks et al. | |

FOREIGN PATENT DOCUMENTS

| | | |
|---|---|---|
| EP | 1947340 A1 | 7/2008 |
| EP | 001156335-0001 | 7/2009 |
| JP | 1385142 | 3/2010 |
| WO | 2008042987 A2 | 4/2008 |

OTHER PUBLICATIONS

Jarnagin et al., "Office Action," for U.S. Appl. No. 13/184,434, dated May 29, 2014.

International Search Report and Written Opinion dated Dec. 22, 2011 from International Patent Application No. PCT/US2011/044279 (WO 2012/009697 A1).

* cited by examiner

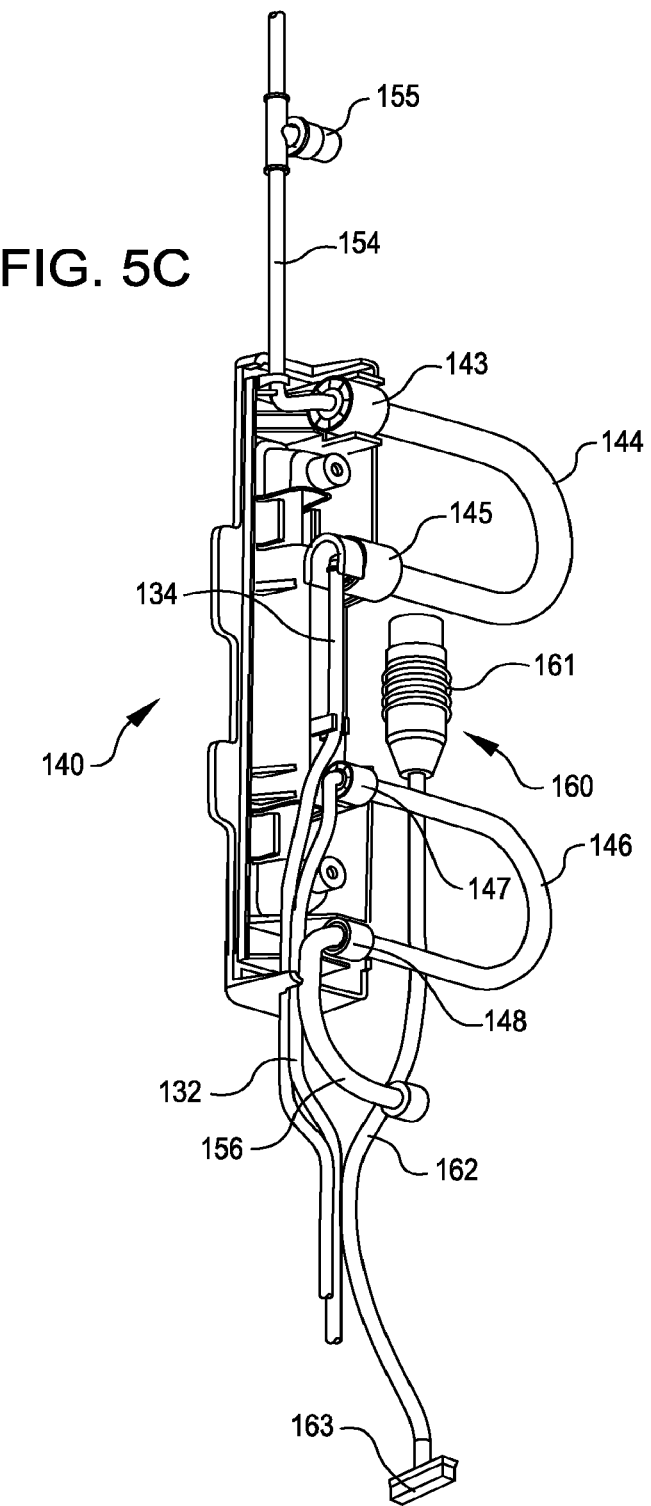

INTERVENTIONAL CATHETER ASSEMBLIES, CONTROL CONSOLES AND ADAPTIVE TUBING CASSETTES

REFERENCE TO PRIORITY APPLICATIONS

This application is a continuation application of U.S. patent application Ser. No. 13/743,173 filed Jan. 16, 2013, now U.S. Pat. No. 9,775,964, which is a divisional application of U.S. patent application Ser. No. 12/854,834 filed Aug. 11, 2010 which claims the benefit of priority under 35 U.S.C. § 119 to U.S. Provisional Patent Application Ser. No. 61/233,434 filed Aug. 12, 2009. The disclosures of these priority applications are incorporated by reference herein in their entirety.

FIELD OF THE INVENTION

The present invention relates generally to interventional catheter operating systems and components for use in a wide range of medical applications. The present invention relates, more particularly, to systems and methods for interfacing and operating a range of interventional catheters having aspiration and/or infusion capabilities with a common interventional catheter operating and control console. Adaptive interface components such as tubing cassettes facilitating communication between interventional catheter assemblies and a common control console, including components providing authentication, security and operating instructions, as well as adaptive tubing cassettes providing an interface between operating systems provided in the control console and various types of interventional catheters, are disclosed.

BACKGROUND OF THE INVENTION

Interventional techniques for removing disease such as atherosclerotic plaque, thrombus and other types of obstructions and partial obstructions from internal body lumens or cavities using interventional catheters are well-established. Interventional catheters may employ operating heads that break down and/or remove occlusive material using mechanical structures such as cutter assemblies, abrasive materials and/or shaped tools, excision devices, ablation instruments employing modalities such as RF, laser or radiation-induced ablation modalities, ultrasound, fluid jets or fluid agitation and the like. Other types of interventional catheters may provide fluid infusion and/or aspiration alone, or in combination with another diagnostic or treatment modality. Many of these systems involve placement of a guiding catheter and/or guide wire prior to introduction of the interventional catheter, facilitating navigation of the interventional catheter to the target operating site and manipulation of the interventional catheter at the target site.

Many material removal devices and interventional catheters incorporate mechanical aspiration systems to remove fluid, disease material and/or particulate debris from the site. Some systems incorporate, or are used in conjunction with, other mechanisms such as distal filters, for preventing material dislodged during the procedure or debris generated during the procedure from circulating in the blood stream. Some interventional catheter systems incorporate or are used in conjunction with a fluid infusion system providing delivery of fluids to an interventional site. Interventional catheter systems may also incorporate or be used in conjunction with imaging systems and other types of complementary and/or auxiliary tools and features that facilitate desirable placement and operation of the system during an interventional procedure.

One or more controllers are generally provided for operating an interventional catheter. Some types of interventional catheters employ a single operational and control component interfacing with and mounted to the interventional catheter at a proximal end of the catheter. In devices that interface with a single operating and control component, system operating components may be housed in the operating and control component, and user interface controls for operating the catheter and operating head are provided on the operating and control component. Various control features for activating and operating the interventional catheter, its aspiration and/or infusion systems, and/or its operating head may be provided. Status indicators, system read-outs and operating information may also be provided on interventional catheter operating and control components.

Some interventional catheter systems employ a console-type controller that interfaces directly with interventional catheter components, while some interventional catheter systems employ both a console-type controller that houses non-disposable components such as pumps, drive systems, electrical, electronic, vacuum and fluid control systems, and the like, as well as another intermediate control device that provides operator control options and, in some cases, feedback information. The intermediate control device is typically located at or near a proximal end of the interventional catheter, and may be positioned within or close to the sterile field during a procedure. Interventional catheter systems employing both a console-type controller and an intermediate control device are described, for example, in PCT International Publication WO 2008/042987 A2, the disclosure of which is incorporated herein by reference in its entirety. Patients may also be monitored during an interventional procedure using separate or integrated systems, such as fluoroscopic or other visualization systems, vital sign monitoring systems, and the like.

During setup of an interventional catheter system employing a control module, an operator typically connects or otherwise operably interfaces components of the interventional catheter assembly, or an intermediate control system generally designed for single patient use, to the reusable console-type control module. In many cases, this involves installing infusion and/or aspiration tubing in the console, interfacing the tubing with pump(s), infusion sources, aspiration receptacles, priming the infusion system, and the like. The operator then navigates the catheter to a desired interventional site and is ready to operate the catheter.

Some interventional catheter systems operate according to pre-set operating parameters and allow the operator to activate and inactivate the device only, without allowing the operator to select or vary operating parameters based on individual patient and intervention conditions. Some interventional catheter systems provide user operable controls that allow an operator to select or vary at least some of the interventional catheter operating parameters. Many interventional catheter systems that employ a rotating operating head, for example, provide an interface permitting the operator to control the rotational speed of the operating head during an interventional procedure. In other interventional catheter systems, control and interface systems are provided to allow the operator to select, set, adjust or otherwise configure various user selectable operating parameters and/or system settings. There may be numerous such user selectable and adjustable operating parameters and/or system settings that may be established and/or selected prior to proceeding with an intervention, or during an intervention. Suitable operating parameters depend on the nature of treatment and the disease or condition state, the patient's anatomy and condition, the specific interventional catheter in use and the operating capabilities of the interventional catheter, and the operator's preferences and expertise.

Technology for providing coded operating information in association with a single use interventional catheter assembly and conveying that coded operating information to a drive unit has been proposed. U.S. Patent Publication 2007/0073233 A1, for example, discloses a thrombectomy catheter deployment system that simplifies set-up procedures in systems employing a disposable thrombectomy pump/catheter assembly that mounts in a stand-alone drive unit for operation. The single use pump catheter system incorporates a plurality of preconnected structures, including a tubular structure, for interfacing with mating structures in the drive unit and for automatic engagement and alignment, or disengagement, of components in the single use pump/catheter assembly with the drive unit. The drive unit uses digital technology to enable multiple operating modes encoded on individual pump/catheter assemblies using barcode or radio frequency identification technology. Operating mode parameters such as pump stroke length, downstroke speed, acceleration time, and the like are encoded on the pump/catheter assembly so that, when it is mounted on the drive unit, calibration and operating mode information is automatically provided to the drive unit.

Surgical systems employing multiple surgical devices having different operational limits that are mountable on and used with a common drive system or handpiece are disclosed, for example, in U.S. Pat. No. 4,705,038 (Re. 34,556). In this system, each surgical device has an indicator on its proximal portion indicating its operational limits, and the handpiece has an automatic sensor (e.g., a magnetic sensor) for detecting and reading the indicator. When the surgical device is mounted on the handpiece and the operational limits are detected, the handpiece operates the motor drive in accordance with the operational limits coded by the surgical device. This allows multiple surgical devices, each having different operating limits and characteristics, to be operated by a common drive and controller.

Similar coding systems have been proposed for use with other types of devices, such as power toothbrushes, may permit the use of multiple detachable brush heads with a common drive housed in a handle. Coding systems for recognizing different brush heads mounted on a common handle have been developed. Systems for conveying data, such as operational data, from the brush head to the handle using RFID technology have also been developed. For example, U.S. Pat. No. 7,024,717 discloses radio signal communication between the handle of a tooth brush and a cleaning tool, and a memory element in the cleaning tool for storing data identifying the cleaning tool and indicating one or more operating parameters.

The present invention is directed to interventional catheter operating systems and adaptive components that allow different types of interventional catheter assemblies to be operated using a common control module and common operating systems. In particular, the present invention provides interventional catheter operating consoles having aspiration and/or infusion systems that can be used with a range of interventional catheters having aspiration and/or infusion capabilities, and to adaptive components such as tubing cassettes and controllers used to interface between the operating console and the interventional catheter.

SUMMARY OF THE INVENTION

The present invention provides interventional catheter assemblies that may be employed to rapidly and effectively aspirate, irrigate, deliver materials to and/or remove unwanted material from body lumens or cavities, control consoles housing operative components for operating interventional catheters, and adaptive interface components such as tubing cassettes and controllers used to provide an interface between interventional catheter assemblies and a common control console. Interventional catheter assemblies, control and operating systems and adaptive components disclosed herein may be adapted for use in a wide variety of interventional procedures within a variety of body lumens or cavities such as blood vessels and vascular cavities, gastrointestinal cavities, lumens or cavities in the urinary system and in male and female reproductive organs, and other fluid cavities such as pulmonary lumens and gas exchange cavities, nasal and sinus cavities and the like.

Interventional catheter assemblies of the present invention may be used, for example, for removing undesired material from native blood vessels such as native coronary, renal, cranial, peripheral and other blood vessels, artificial or grafted vessels such as saphenous vein grafts, and the like. The lumen may have implanted devices such as stents or ports in place. Undesired material that is removed using interventional catheter assemblies and control systems disclosed herein may be disease material such as atherosclerotic plaque, calcified plaque, thrombus, or other types of deposits, gallstones, a valve or portion thereof, undesired fluids, and the like. Fluids delivered to a desired target site may include saline and other biocompatible fluids, diagnostic or therapeutic agents, fluoroscopic and other imaging agents, and the like. Tools and materials delivered to a desired target site may include implantable devices, interventional devices, visualization tools, micro-surgical tools, and the like. In certain circumstances, interventional catheters disclosed herein are employed in the treatment of cardiovascular or peripheral artery disease to remove disease material from blood vessels, including peripheral blood vessels.

Interventional catheter assemblies generally include an elongated, flexible catheter component that is at least partially inserted into and navigated within a patient's body, through lumens and/or cavities, while an operator controls the system externally of the patient's body. The interventional catheter assembly may be navigated to a desired interventional site over a guide wire or using a guiding catheter or sheath assembly. Many of the interventional catheters disclosed herein incorporate a component that is operable by a user when positioned at or near a target intervention site, referred to herein as an "operating head," which is generally positioned at or near the distal end of the interventional catheter. The interventional catheter assembly interfaces, at a proximal portion that remains outside the body, with a control module or another controller by means of fluidic connections (using, e.g., infusion and/or aspiration tubing), electronic connections, electrical connections, wireless communications protocols, and the like.

As used herein, "proximal" refers to a direction toward the system controls and the operator along the path of the catheter system, and "distal" refers to the direction away from the system controls and the operator along the path of the catheter system toward or beyond a terminal end of the operating head.

In some embodiments, an operating head, or a component of an operating head, may be operably connected to a rotatable and/or axially translatable drive shaft, drive system and one or more control systems. A rotatable operating head may incorporate one or more cutter or ablation elements. In some embodiments, an operating head may comprise an abrasive surface or an abrasive material provided on a surface of a rotational element. In alternative embodiments, the operating head may comprise another type of material removal device, such as a plaque excision device, a laser ablation or high frequency ultrasound ablation device, or a radio frequency or heat-producing or electrical device that operates to remove unwanted material from body lumens or cavities and generally does not rotate during operation. An operating head may be advanced by operator manipulation or by mechanical systems, or by a variety of other systems, including electrical systems, radio frequency, stereotactic and other remotely controlled systems. The operating head may incorporate aspiration and/or infusion features, device or tool delivery features, material removal features and the like, and may provide additional functionalities such as ultrasound guidance (or guidance using another modality), various types of visualization and imaging features, and the like.

Fluidic communication between a distal portion of the interventional catheter and/or an operating head and externally positioned components of the interventional catheter assembly may be provided through one or more sealed passageways of the catheter system. Sealed aspiration and/or infusion lumens provided in the interventional catheter assembly generally interface with aspiration and/or infusion tubing, which in turn interfaces with aspiration and/or infusion systems, such as pumps, vacuum devices, infusate sources, and the like, provided in connection with operating and control systems. Communication systems or pathways may also be provided for delivery of power, for rotationally driving (or otherwise operating) and/or translating an operating head, for implementing various control features, and the like. The system components described below are described as exemplary components and are not intended to limit the scope of the invention.

A control console is generally provided as a reusable system that houses certain interventional catheter assembly operating systems, such as aspiration and/or infusion systems, and interfaces with an interventional catheter to provide suitable aspiration and/or infusion pressures to appropriate interventional catheter lumens, to provide power to the interventional catheter as necessary, and the like. The interventional catheter aspiration and infusion lumens generally communicate with and terminate proximally in aspiration and infusion tubing, which interfaces with aspiration and infusion systems in the console and infusion reservoirs and aspirate receptacles provided externally of the interventional catheter.

The present invention contemplates a family of interventional catheters having different operating capabilities, features and parameters that may be operated on a common control console. In many embodiments, interventional catheter assemblies are provided as single use devices that interface with a reusable control console. The catheter assemblies are typically provided as sterile devices and are operated in the sterile field during an intervention, while the control console is generally used outside the sterile field. The control console may be provided as a stationary, table-top type device; it may be mounted on a portable platform such as a cart or IV pole or the like; or it may be provided as a system integrated with other interventional or patient monitoring systems.

In general, the present invention provides interventional catheter assemblies and adaptive interface components for operating and controlling interventional catheter assemblies having aspiration and/or infusion and/or operating head capabilities using a common control console housing aspiration and/or infusion and/or operating head drive systems. A common control console may thus be used to operate an aspirating interventional catheter, such as a thrombectomy device, as well as a simple infusion catheter, as well as atherectomy and thrombectomy devices that operate using either or both aspiration and infusion systems. The control console may also incorporate other operating and control features, drive systems, power supplies, and the like, that may interface with an interventional catheter assembly.

Instructions for operating an interventional catheter assembly using operating and control systems (e.g., infusion and/or aspiration systems) provided in an independent control console may be predetermined and may be provided on or encoded in an instructional component associated with each interventional catheter assembly. In one aspect, interventional catheter assemblies of the present invention comprise operating instructions encoded within the interventional catheter assembly that are communicated to and effectuated by the control console when the interventional catheter is interfaced with the control console. In this scheme, interventional catheter assemblies having a range of operating capabilities and optional operating characteristics may be operated in accordance with operating parameters, protocols, and the like, specified by operating instructions encoded in each interventional catheter assembly. In one embodiment, operating instructions are stored in a memory device, such as an EEPROM, associated with the interventional catheter assembly and communicated to the control console when the interventional catheter assembly is electrically connected to a control console. It will be appreciated that other types of memory and electronic storage devices may be used for storing operating instructions and communicating them to a control console.

Memory and storage devices containing operating instructions for operation of interventional catheter assemblies may alternatively be provided on discrete adaptive interface components, such as dongles or other types of storage devices, that may interface with either the control console or the interventional catheter assembly, or both, to communicate operating information to the control console.

In another aspect, multiple instruction sets for operating different interventional catheter assemblies, or for operating common interventional catheter assemblies according to different operating protocols, are provided in an electronic memory or storage device associated with the interventional catheter assembly, or the control console, or an adaptive interface component and, when an interventional catheter assembly is interfaced with a control console, a detection system identifies the type and capabilities of the interventional catheter assembly and, based on that detection, selects operating instructions tailored to the interventional catheter assembly. In another embodiment, a detection system identifies the type and capabilities of the interventional catheter assembly and provides a menu of potential operating protocols, or prompts a user to select from among multiple matching operating protocols. These embodiments are described for illustrative purposes; it will be appreciated that many different control and detection schemes may be provided for operating interventional catheter assemblies having different capabilities or operating protocols on a common control module.

In one aspect, interventional catheters of the present invention may have authentication features encoded within the interventional catheter assembly that interface with a control console to authenticate the interventional catheter for use on the control console and, upon a successful authentication, allow operation of the interventional catheter on the control console. Authentication protocols may additionally be provided to allow operation by authorized operators, and to communicate operating instructions, parameters, limits, and the like, to the control console.

The control console receives instructions from the interventional catheter system or an auxiliary device and, provided an authentication protocol is successfully executed, operates the interventional catheter assembly accordingly. The control console may interface with and operate many different interventional catheter devices having different operating capabilities and parameters. Instructions may also be provided for operating interventional catheter assemblies having the same or similar operating capabilities according to different operating parameters, as well as multiple and different sets of operating parameters, depending on the device or interventional catheter system being used and interfacing with the console.

In another aspect, adaptive components such as tubing cassettes having various configurations are provided for operating different types of interventional catheters on a common control console. In one embodiment, for example, a tubing cassette having a housing through which aspiration and/or infusion tubing is conveyed, is provided for interfacing with aspiration and/or infusion systems provided on a control console. The tubing cassette may route aspiration and/or infusion tubing in a predetermined configuration to mate with aspiration and/or infusion systems in the control console, and may also mate with a mechanical interface provided on the control console to provide stable mounting of the tubing cassette during an intervention. The tubing cassettes are preferably provided as part of and integrated with the interventional catheter assembly.

For control consoles incorporating peristaltic pumps as aspiration and/or infusion systems, for example, adaptive tubing cassettes comprising a housing component and one or more tubing loops sized and configured for mating with a tubing pathway in a peristaltic pump are provided. Adaptive tubing cassettes are designed to position the aspiration and/or infusion tubing between the pump rollers, facilitating loading of the fluid tubing providing fluidic communication with the interventional catheter assembly on the control console.

The size, configuration, composition and positioning of the tubing loop(s) may be selected based on the type of aspiration and/or infusion system used, desired pump configurations, operating infusion and/or aspiration volumes and pressures, and the like. In one embodiment, adaptive tubing cassettes provide tubing loops for interfacing with both of the infusion and aspiration systems provided on the control console; in alternative embodiments, adaptive tubing cassettes may provide a single tubing loop for interfacing with only the infusion system or the aspiration system, depending on the capabilities of the interventional catheter assembly.

BRIEF DESCRIPTION OF THE DRAWINGS

FIG. 5C shows a perspective view of the exemplary interventional catheter tubing cassette of FIG. 5A with a portion of the housing removed to illustrate the interior of the tubing cassette.

Like numbers have been used to designate like parts throughout the several drawings to provide a clear understanding of the relationship of the various components and features, even though different views are shown. It will be understood that the appended drawings are not necessarily to scale, and that they present a simplified, schematic view of many aspects of systems and components of the present invention. Specific design features, including dimensions, orientations, locations and configurations of various illustrated components may be modified, for example, for use in various intended applications and environments.

DETAILED DESCRIPTION

Figure 1:
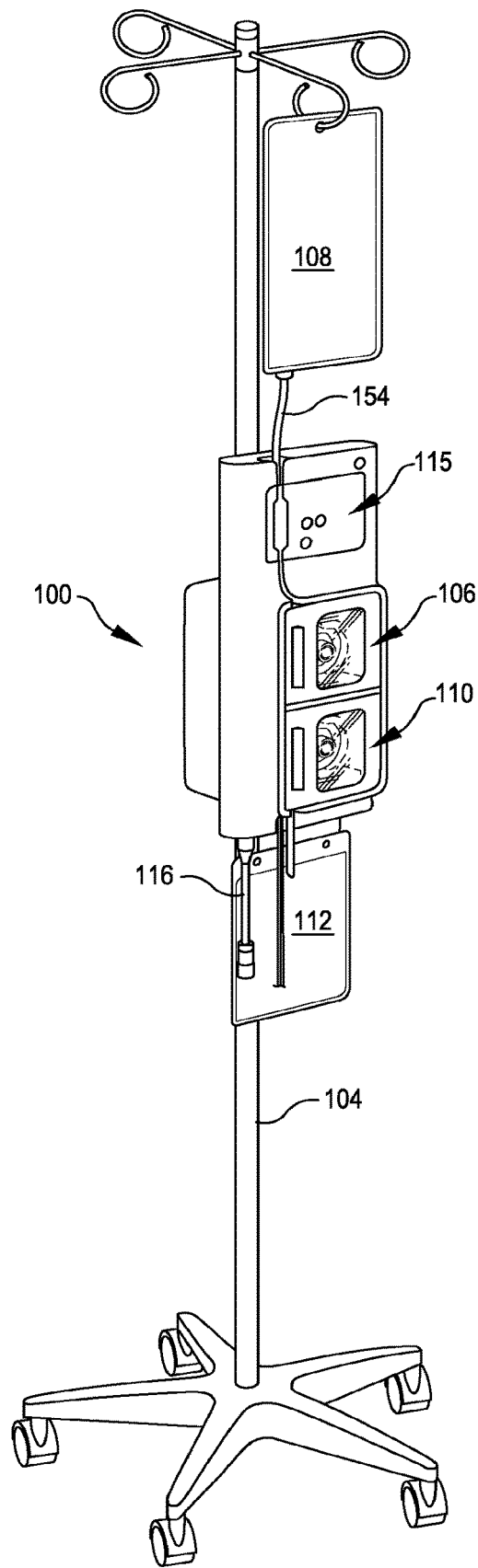
FIG. 1 shows a schematic view of an exemplary interventional catheter control console of the present invention comprising aspiration and infusion systems and showing an infusion source and an aspiration receptacle.

FIG. 1 illustrates an exemplary interventional control console 100 mounted, with an accessory infusate reservoir and aspirate receptacle, on a portable IV pole platform 104. In the embodiment illustrated in FIG. 1, control console 100 incorporates an infusion system 106 in fluid communication with an infusate source reservoir 108, such as a sealed fluid bag, and an aspiration system 110 in fluid communication with an aspirate collection receptacle 112. In the embodiment illustrated, and in preferred embodiments, at least one, and preferably both of the infusion and aspiration systems comprise peristaltic pumps arranged in a vertically stacked relationship. In one preferred embodiment, infusion system 106 comprises a high pressure peristaltic pump capable of infusing fluid at a rate of up to 120 ml/min at a pressure of about 160 psi. In another preferred embodiment, aspiration system 110 comprises a generally lower pressure peristaltic pump capable of aspirating liquid and/or liquid/solids mixtures at a rate of up to 70 ml/min at a pressure of about 15 psi.

Control console 100 may house other system operating systems and components as well, and typically houses complex or bulky operating and control systems that are impractical to provide in single use interventional catheter assemblies, or that cannot be readily sterilized. Control console 100 generally draws power from an external electrical system and generally incorporates a control panel 115 providing a user interface for interacting with operating and control systems housed in control console 100, and for monitoring system operating conditions. In one embodiment, control panel 115 provides a key pad interface for user selection of selectable options and LED indicators for displaying device operational status. Electrical cable 116 may provide electrical power from the control console 100 to the interventional catheter assembly when interfaced.

Figure 2:
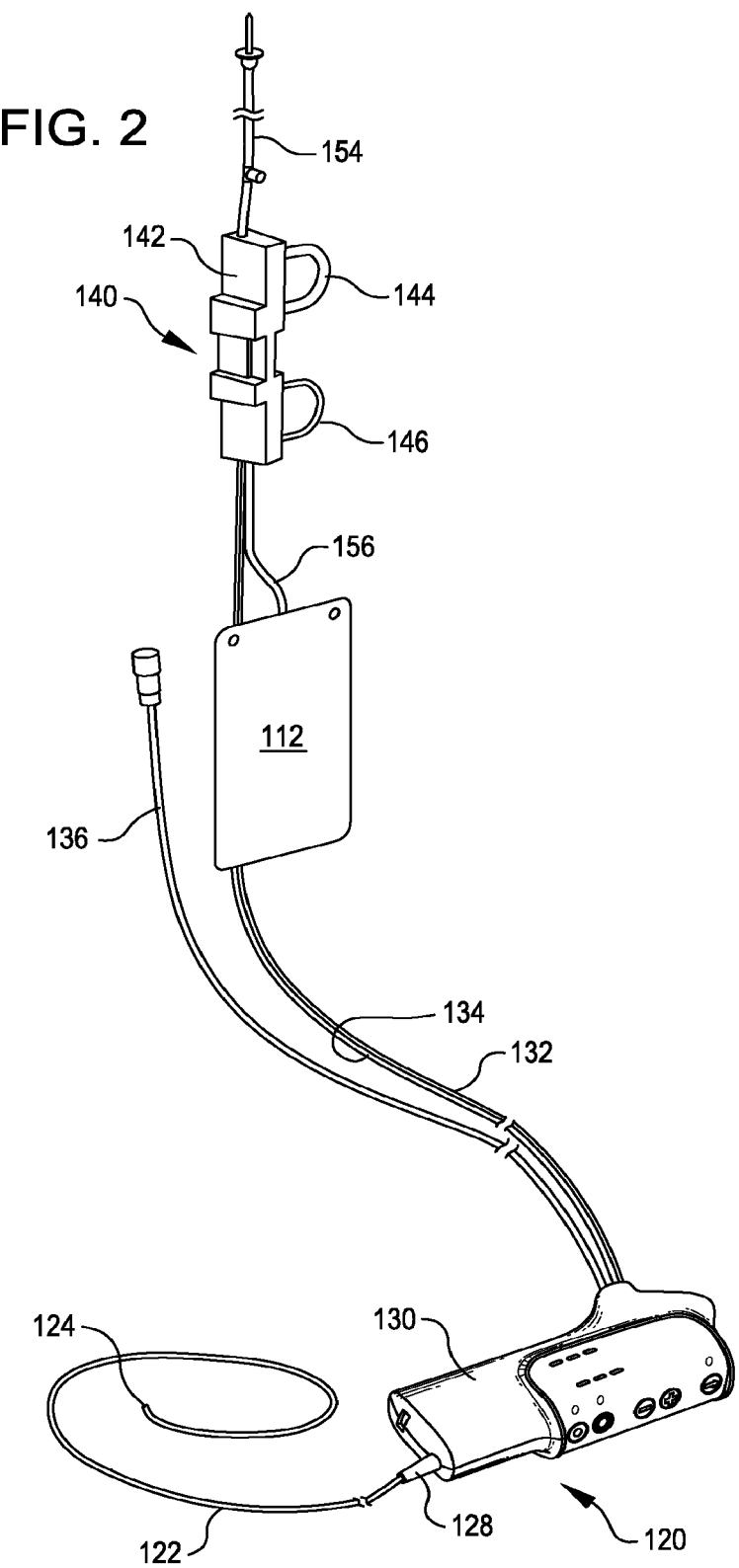
FIG. 2 shows a schematic view of an interventional catheter assembly incorporating an adaptive tubing cassette that mates with and stably mounts to aspiration and infusion systems incorporated in a control console as illustrated in FIG. 1.

FIG. 2 schematically illustrates an interventional catheter assembly suitable for use with the control console illustrated in FIG. 1. Simple interventional catheter systems may provide aspiration and/or infusion functions, providing fluids to a desired interventional site using an infusion system and/or removing fluid and debris from an interventional site using an aspiration system. More complex interventional catheter systems may incorporate an operating head provided in proximity to a distal end of the interventional catheter and communicating with a material removal or ablation operating system located in an intermediate housing assembly or in a control console. Interventional catheter assembly 120, as illustrated in FIG. 2, comprises an elongated, flexible catheter 122 sized and configured for insertion into a patient, the catheter having an operating head 124 positioned in proximity to a distal end of the catheter. Operating head 124 may be mounted, directly or indirectly on the catheter and/or on a drive system that transits the catheter.

Interventional catheter 122 may also incorporate aspiration and/or infusion lumens or channels providing fluidic communication between a distal end of the interventional catheter positioned at a site of intervention and externally positioned aspiration and/or infusion components of the interventional catheter and a control console. Interventional catheter 122 is typically mounted to, or associated with, a housing assembly 130 at a proximal end of the interventional catheter, such as at feedthrough 128. In the embodiment illustrated in FIG. 2, interventional catheter housing assembly 130 may incorporate drive system(s) for operating and controlling the operating head, as well as fluid management systems providing sealed communication between aspiration and/or infusion lumens in interventional catheter 122 and aspiration and infusion tubing 132, 134, respectively, that exits the housing assembly 130 and interfaces with aspiration and/or infusion systems on a control module. Electrical and electronic communication between housing assembly 130 and a control module may be provided by the connection of electrical cable 136 to the control module.

The interventional catheter assembly may additionally comprise an adaptive tubing cassette 140 that interfaces with the aspiration and/or infusion systems provided in a control module. In the embodiment illustrated in FIG. 2, adaptive tubing cassette 140 comprises a housing component 142 and two preformed tubing loops 144, 146 sized and configured to insert into and mate with infusion and aspiration systems housed in the control console. Tubing loops 144, 146, in the embodiment shown, are sized and configured to insert into and mate with a tubing pathway, or occlusion bed, provided in peristaltic pumps housed in the control console. Infusion tubing loop 144 is in fluid communication with interventional catheter assembly infusion tubing 134 and an infusion lumen in catheter 122, as well as infusate source tubing 154, which is connected or connectable to an infusate source or reservoir. Aspiration tubing loop 146 is in fluid communication with interventional catheter assembly aspiration tubing 132 and an aspiration lumen in catheter 122, as well as aspirate tubing 156 connected or connectable to aspirate collection receptacle 112. Adaptive tubing cassette housing component 142 provides a structure for grasping and manipulation by an operator and also incorporates an interface structure sized and configured to mate, such as mechanically and/or electronically, with a receiving structure provided on the control console in proximity to the aspiration and/or infusion systems.

Figure 3:
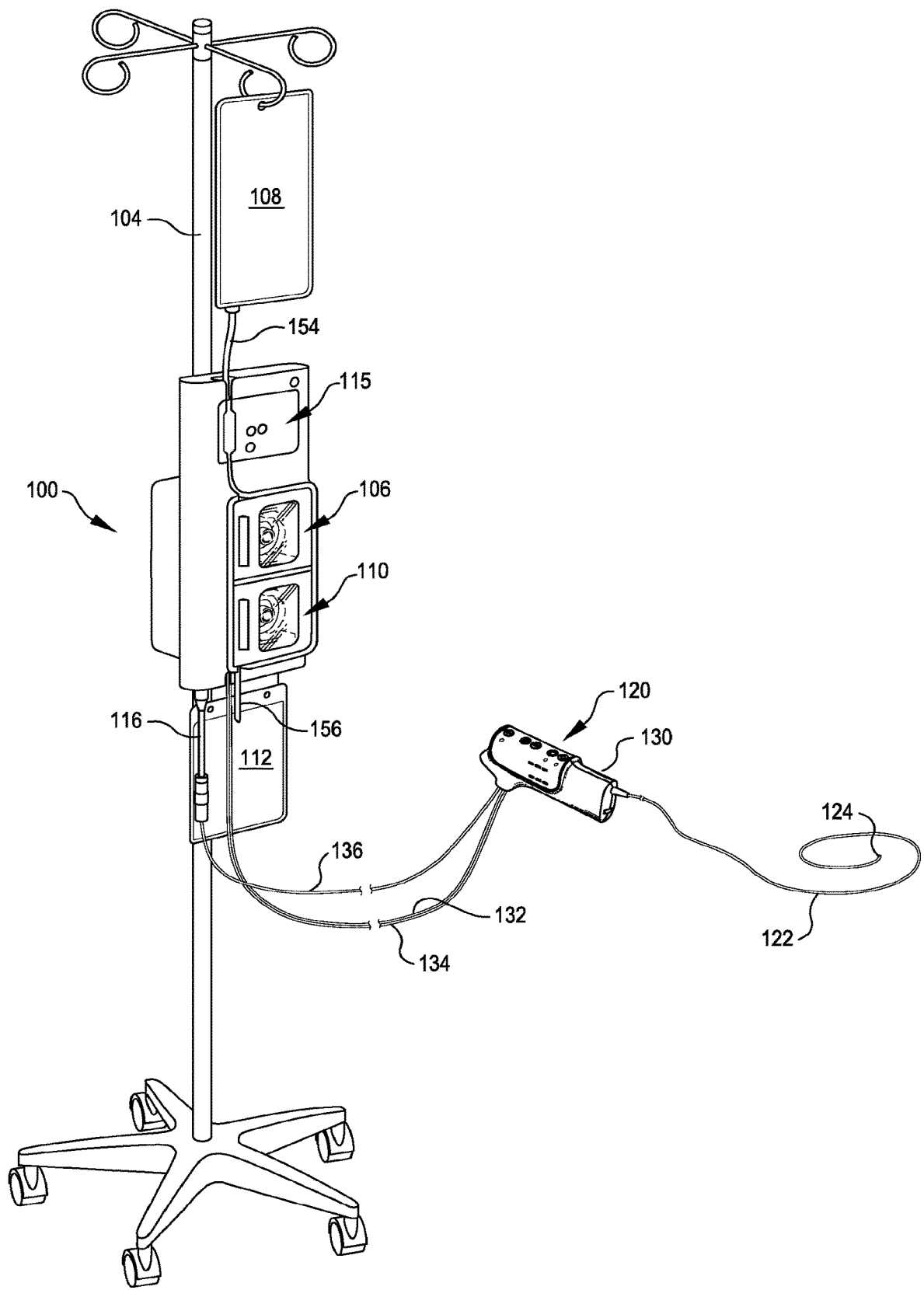
FIG. 3 illustrates an interventional catheter assembly of FIG. 2 mounted on a control console of FIG. 1.

FIG. 3 illustrates an exemplary interventional catheter assembly 120 mounted on a control console 100. In this view, an adaptive tubing cassette is mounted on the control console, with infusion and aspiration tubing loops operably mounted on infusion and aspiration systems 106, 110, respectively. Infusion and aspiration systems 106 and 110 are provided in enclosed spaces in the control console illustrated schematically in FIG. 3 and, when the adaptive tubing cassette is mounted on the console, doors or other structures enclose and protect the infusion and aspiration systems during operation of the control console and interventional catheter assembly. The fluid infusion pathway extends from infusate source 108, which is operably connected to infusion tubing 154, which in turn operably connects to infusion tubing loop 144 of the adaptive tubing cassette 140, and from there to interventional catheter infusion tubing 134, to an infusion lumen in catheter 122. The aspiration pathway is established, in reverse, from an aspiration lumen in catheter 122, through aspiration tubing 132, aspirate tubing loop 146, aspirate tubing 156 and aspirate collection receptacle 112.

As shown in FIG. 3, control console electrical cable 116 and interventional catheter electrical cable 136 may be connected to provide electrical and electronic communication between the systems, and to provide power from the control console (and an external power source) to interventional catheter assembly 120. Connection of cables 136 and 116 may also establish communications pathways between an interventional catheter assembly and the control console, and may initiate an authentication process and/or a detection process as described below.

Interfacing an interventional catheter assembly 120 with a control console 100 may initiate the communication of data, instructions, coded information, or the like, between the interventional catheter assembly 120 and control console 100. In one embodiment, the data communicated may include operating instructions, such as operating parameters, encoded within the interventional catheter assembly that are used by the control console to operate the interventional catheter assembly according to the instructions provided. In this type of system, control instructions may be encoded, for example, in hardware, firmware or software associated with each interventional catheter. In some embodiments, control instructions may be encoded in a non-volatile memory element, such as ROM, EEPROM, and/or flash memory elements associated with the interventional catheter. In one embodiment, nonvolatile memory element(s) may be permanently associated with, such as embedded or permanently mounted in, each interventional catheter assembly.

In another embodiment, the data encoded in the interventional catheter assembly and communicated to the control console includes an authentication protocol to confirm and verify the suitability of an interventional catheter assembly, or to confirm and verify the suitability of instructions encoded by the interventional catheter assembly, for use on a particular control console. Authentication protocols may require both the console and the interventional catheter to be satisfactorily authenticated prior to operation of the console and initiation of an interventional procedure. A variety of known authentication protocols may be implemented.

Authentication devices may be provided, for example, as two-interface security tokens with transient data flow that does not interfere with other instructional functions and communications interfaces. In some embodiments, the control console may be configured to run only in a restricted mode, or not at all, absent satisfactory completion of an authentication protocol. These types of security devices may be used to control the use of interventional catheters with particular control consoles, and to "lock out" unauthorized interventional catheter devices from being used with certain control consoles. In some embodiments, control console 100 may incorporate a cyclic redundancy check (CRC) that detects an interventional catheter assembly identification code to verify that the interventional catheter assembly, and the encoded parameter set, is authorized, and allow the control console to proceed to operational setup and implement operating protocols.

In alternative embodiments, authentication features and/or operating instructions may be provided on adaptive components, such as electronic devices, that are provided and used separately from the interventional catheter and that may be authenticated by both the interventional device and the control console to communicate operating instructions, parameters, limits, and the like, to the control console depending on the type of interventional catheter being used. Non-volatile memory elements, for example, may be associated with or housed in an auxiliary control device such as a hardware or flash memory device, or a dongle, having an interface, such as a port, that interfaces directly with the control console and encodes operating instructions, operating parameters and/or limits for one or more different interventional catheter assemblies. Auxiliary control devices such as dongles may be used both as security/authentication devices and to provide operating instructions to the control console.

The control console detects operating instructions encoded in the interventional catheter assembly or an auxiliary device and, provided the authentication protocol was successful, operates the interventional catheter assembly accordingly. The control console may interface with and operate many different interventional catheter devices, having different operating capabilities and parameters. Instructions may also be provided for operating interventional catheter assemblies having the same or similar operating capabilities according to different operating parameters, as well as multiple and different sets of operating parameters, depending on the interventional catheter system being used and interfacing with the console. Parameter sets, authentication protocols, and the like may be changed or updated by means of software, firmware or hardware updates.

Many different operational control features and parameters relating to infusion and/or aspiration may be encoded using systems and methods of the present invention. Exemplary aspiration parameters include, for example: aspiration: yes/no; max aspiration rate limits; min aspiration rate limits; specified aspiration rates; max aspiration volume limits; min aspiration volume limits; specified aspiration volumes; aspiration rate and/or aspiration rate profiles over time; aspiration volume and/or aspiration volume profiles over time; setpoint notifications and alarms (e.g. notification or alarm if aspiration exceeds a setpoint rate or volume or fails to meet a setpoint rate or volume, if the temperature exceeds a setpoint, or the like. Exemplary infusion parameters include, for example: infusion—yes/no; infusion source identifier (if multiple sources); max infusion rate limits; min infusion rate limits; specified infusion rates; max infusion volume limits; min infusion volume limits; specified infusion volumes; infusion rate and/or infusion rate profiles over time; infusion volume and/or infusion volume profiles over time; setpoint notifications and alarms (e.g. notification or alarm if infusion exceeds a setpoint rate or volume or fails to meet a setpoint rate or volume, if the temperature exceeds a setpoint, or the like.

Control consoles may also house operating and control systems providing operation and/or control of an operating head. The following operational control features and parameters relating to operating head function are exemplary of the operating head control features and parameters that may be encoded: Operating head: yes/no; if yes, then type/modality: rotational: yes/no; if yes, then single or multi-mode (e.g. fixed or 30 expandable); other types/modalities (alternatively or in addition)—e.g. u/s, radiation ablation, heat, imaging, etc.; max and min operating parameters; operating parameter(s) and/or parameter profile over time; notifications/alarms, etc. If the interventional catheter assembly incorporates a rotational operating head, the following operational parameters may be encoded: Rotational drive—yes/no; direction—forward/reverse; operating rpm and/or operating rpm over time; notification/alarms. Rotational drive control may be 5 exerted by max, min voltages, voltage profiles during operation, max/min current and current limits, etc. If the interventional catheter assembly incorporates a translational drive, the following operational parameters may be encoded: Translational drive—yes/no; direction—forward/reverse; operating velocity or movement parameters and profiles—e.g. mm or cm/unit time; notifications/alarms, etc. On/off timing and delays for operation 10 of various components and operations may also be incorporated.

In one specific embodiment in which the interventional catheter assembly comprises a rotatable atherectomy device having infusion and aspiration capability and an operating head operable in multiple operating modes, the following operating parameters may be encoded: interventional catheter type/code; interventional catheter version; maximum drive voltage in each of multiple operating modes; minimum drive voltage in each of multiple operating modes; initial drive voltage in each of multiple operating modes; set speed at maximum voltage in each of multiple operating modes; current limits in each of multiple operating modes; infusion pump speeds in each of multiple operating modes; aspiration pump speeds in each of multiple operating modes; infusion pump turn off delay; aspiration pump turn off delay; infusion prime duration; tachometer ratio; infusion pump reverse mode turn off delay; aspiration pump reverse mode turn off delay; reverse mode set voltage and reverse mode direction. It will be appreciated that many other operating control parameters may be adopted and incorporated in methods and systems of the present invention.

Figure 4A:
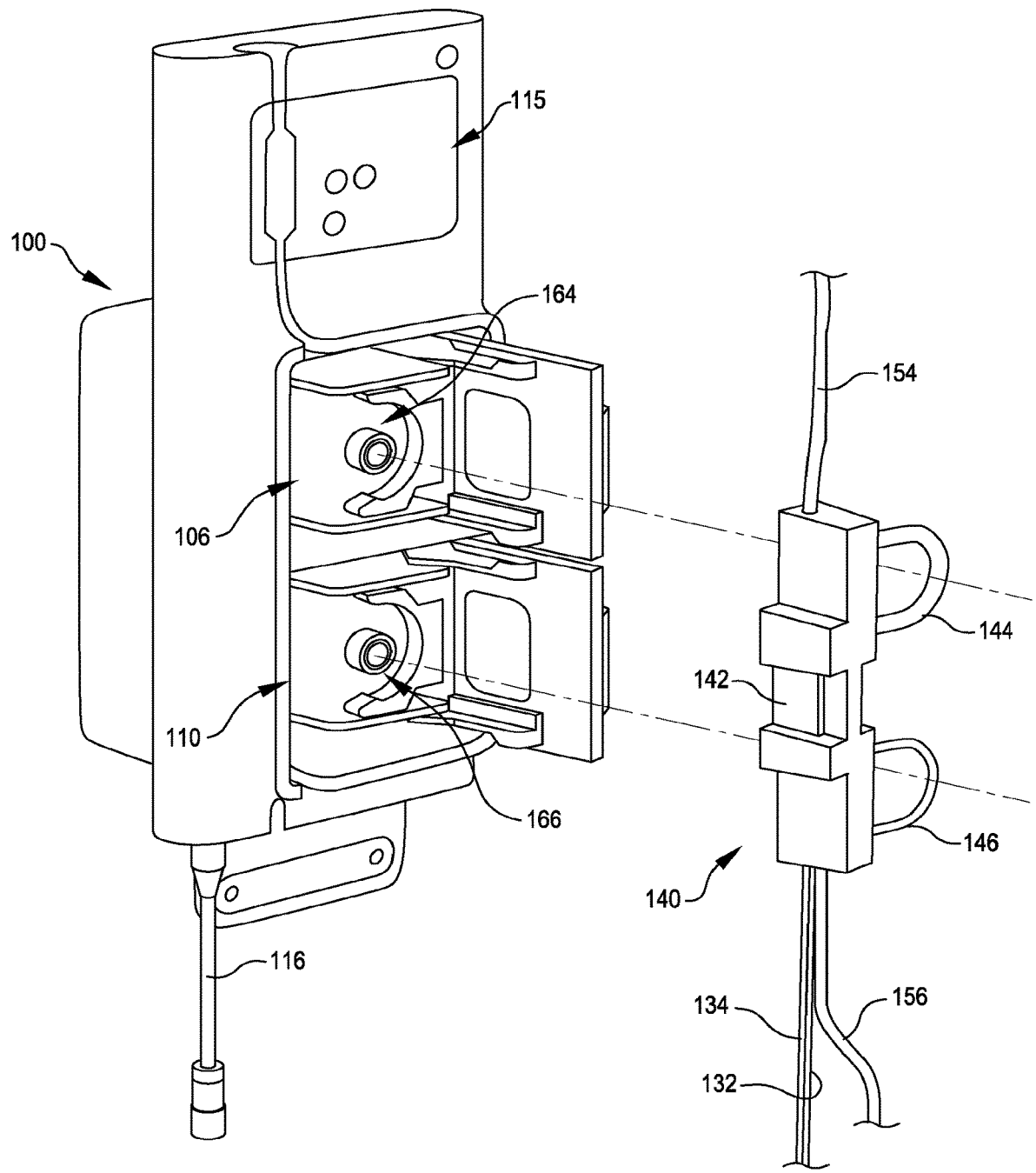
FIG. 4A shows a schematic view illustrating the interface of an adaptive tubing cassette with aspiration and infusion systems incorporated in a control console as illustrated in FIG. 1.
Figure 4B:
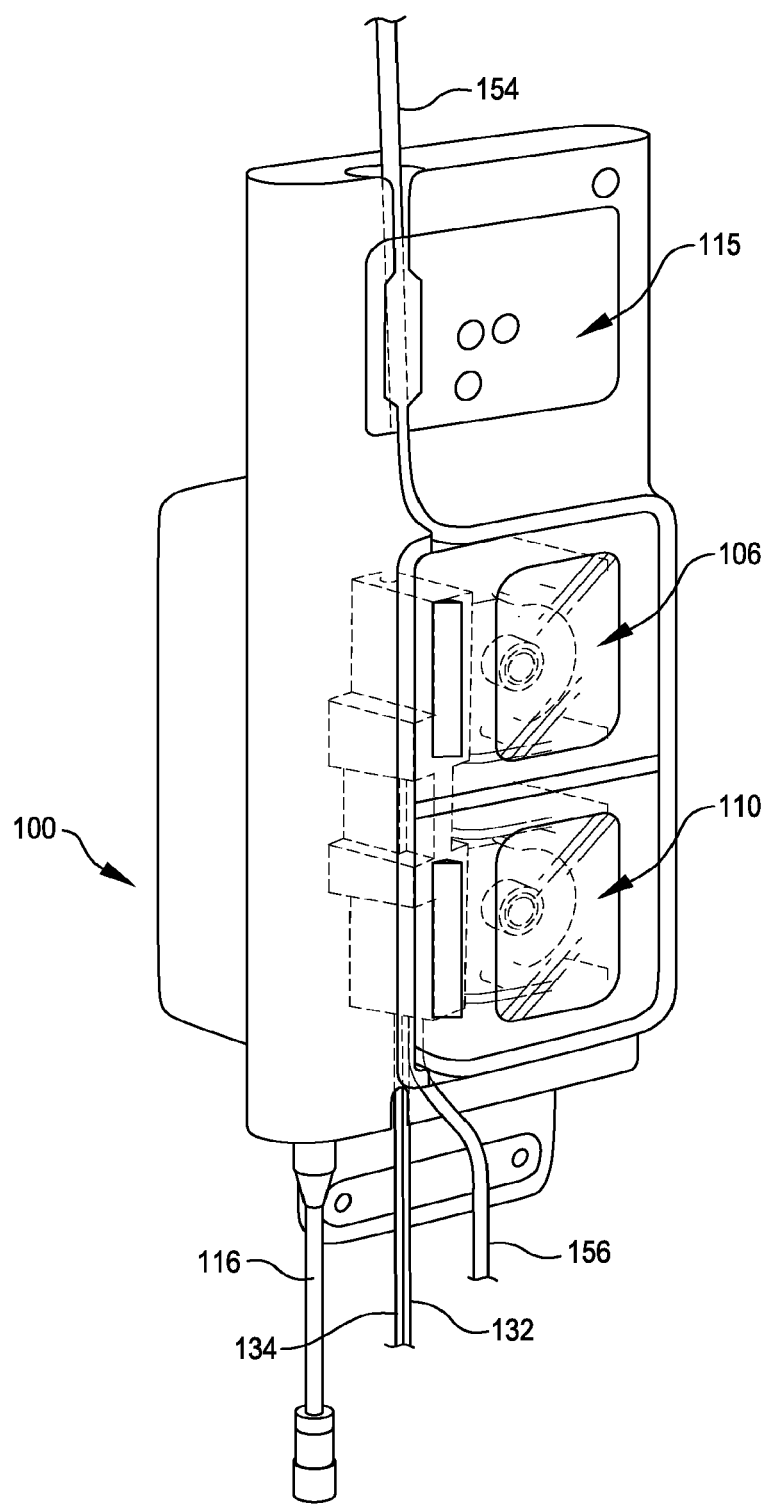
FIG. 4B shows another schematic view illustrating the adaptive tubing cassette shown in FIG. 4A stably mounted in aspiration and infusion systems incorporated in the control console, with exterior doors closed.
Figure 5A:
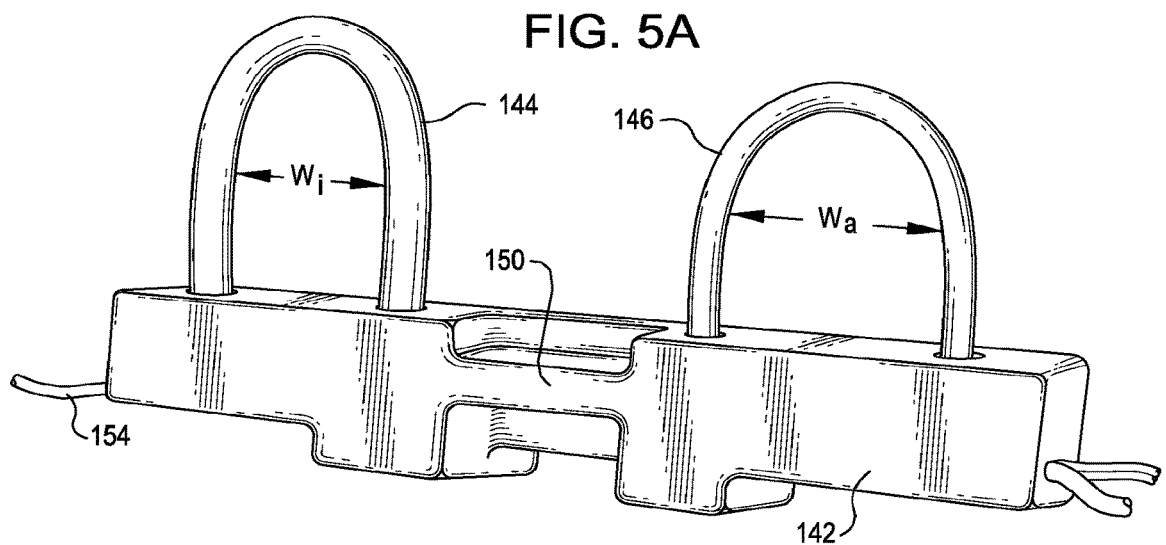
FIG. 5A shows a side perspective view of an exemplary interventional catheter tubing cassette adapted for mating with and stably mounting to aspiration and infusion systems incorporated in a control console.
Figure 5B:
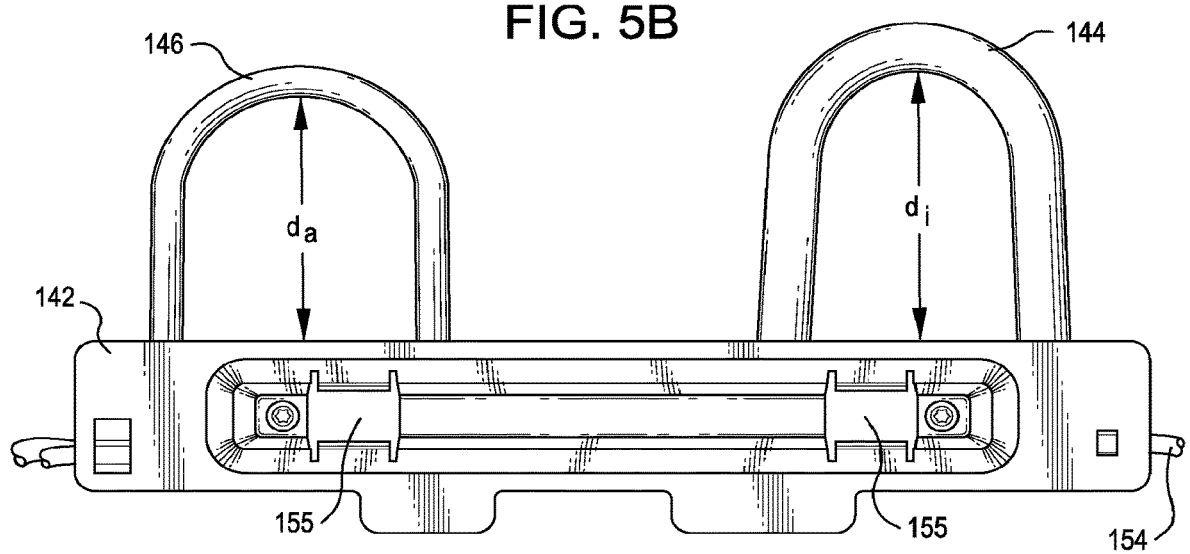
FIG. 5B shows another side view of the exemplary interventional catheter tubing cassette of FIG. 5A illustrating a mechanical mating system for mounting the tubing cassette in a mating receiving structure provided in the console in connection with the aspiration and infusion systems.

FIGS. 4A and 4B show enlarged schematic diagrams illustrating an adaptive tubing cassette 140 in position for mounting (FIG. 4A) and mounted (FIG. 4B) in infusion and aspiration systems on control console 100, and FIGS. 5A-5C show various views of adaptive tubing cassette 140. During operation of the interventional catheter assembly, infusion tubing 154 accesses the infusate source(s) and, prior to entry into tubing cassette housing 142, may incorporate an optional valve 155 (See, e.g., FIG. 5C) comprising a self sealing membrane for withdrawing fluids (or gas) from the infusion tubing line 154, or for introducing fluids to the infusion tubing line 154. Suitable bubble detector(s) may also be provided in conjunction with infusion tubing to detect and/or prevent entrainment of bubbles that would be harmful to patients. Infusion tubing 154 is in sealed fluidic communication with preformed infusion tubing loop 144 at an infusate entry portion 143 of preformed infusion tubing loop 144, and infusion tubing loop 144 is in sealed fluidic communication with interventional catheter infusion tubing 134 at an infusate exit portion 145 of preformed infusion tubing loop 144.

In some embodiments, infusion tubing 154, preformed infusion tubing loop 144 and interventional catheter infusion tubing 134 may comprise tubing having the same or similar properties and dimensions. In other embodiments, such as when infusion system 106 comprises a high pressure infusion pump, preformed infusion tubing loop 144 comprises a thicker walled, generally stiffer tubing material than the tubing of infusion tubing 154 or 134. Preformed infusion tubing loop 144 is configured to mate with a tubing pathway 164 in infusion system 106, which is generally provided as a peristaltic pump occlusion bed that, when the pump is operating, retains the tubing as pump rollers operate to advance infusate through the tubing at a generally high pressure and volume. In one embodiment, desired infusate rates of up to about 120 ml/min at infusate pressures of up to 160 psi are provided by infusion pump system 106. Preformed infusion tubing loop 144 is designed to withstand the generally high infusate pressures generated at infusion pump system 106.

Interventional catheter aspiration tubing 132 is in sealed fluidic communication with preformed aspiration tubing loop 146 at an aspiration entry portion 147 of preformed aspiration tubing loop 146, and aspiration tubing loop 146 is in sealed fluidic communication with aspiration tubing 156 at an aspiration exit portion 148 of preformed aspiration tubing loop 146. Aspiration tubing 156 may be in sealed fluidic communication with an aspirate collection receptacle 112, such as a flexible sealed bag or another sealed collection receptacle. Aspiration tubing loop 146 is configured to mate with a tubing pathway 166 in aspiration system 110, which is generally provided as a peristaltic pump occlusion bed that, when the pump is operating, retains the tubing as pump rollers operate to advance aspirate through the tubing at generally moderate pressures and volumes. In one embodiment, desired aspiration rates of up to about 70 ml/min at aspiration pressures of up to 20 psi are provided by infusion pump system 106.

In some embodiments, aspiration tubing 156, preformed aspiration tubing loop 146 and interventional catheter aspiration tubing 132 may comprise tubing having the same or similar properties and dimensions. In general, aspiration system 110 comprises a low pressure peristaltic pump that, during operation, is capable of pumping aspirate though the system at a rate of about 70 ml/min at a pressure of about 20 psi. Preformed aspiration tubing loop 146 generally comprises a thinner walled, generally more flexible tubing than preformed infusion tubing loop 144.

In some embodiments, preformed tubing loops 144 and 146 comprise different tubing materials and have a different configuration, as shown. As can be seen in FIGS. 5A and 5B, for example, the outer diameter of preformed infusion tubing loop 144 is larger than the outer diameter of preformed aspiration tubing loop 146. In addition, preformed infusion tubing loop 144 extends a greater distance $d_i$ from an edge of housing 142 than the distance $d_a$ of preformed aspiration tubing loop 146 from an edge of housing 142. The width of preformed infusion tubing loop 144 $w_i$ may also be less than the width $w_a$ of preformed aspiration tubing loop 146.

Tubing cassette housing 142 has a size and configuration suitable for housing the various infusate and aspirate tubing components in a convenient and kink-free manner and provides a convenient exposed user grasping surface. The user grasping surface may incorporate a handle 150 in a central portion of the housing, between preformed tubing loops 144 and 146 and oriented for grasping on a surface substantially orthogonal to the plane of the preformed tubing loops. Handle 150 may be formed by adjacent recesses, or indentations, providing convenient access and grasping.

The face of tubing cassette housing 142 generally opposite handle 150, which is substantially orthogonal to the plane of preformed tubing loops on the opposite side, preferably incorporates at least one mechanism for detachably mating with the control console in the area of the infusion and/or aspiration systems. This mating system may comprise a mechanical mating structure(s) provided on tubing cassette housing 142 such as keyed recesses 155, sized and configured to interlock with mating structures provided on the control console in proximity to infusion and aspiration systems 106, 110, respectively. Keyed recesses 155 and the mating structures provided on the control console provide a stable, and preferably detachable mounting of tubing cassette housing 142 on the control console. While mechanically interlocking structures are illustrated and described, it will be appreciated that other types of mechanical and/or electronic structures may provide the desired detachable interlocking features.

FIG. 5C illustrates, in addition to the various fluid tubing components residing in adaptive tubing cassette 140, an electrical or electronic interface component 160. Electronic interface component 160 may comprise a data storage device 161 providing authentication and/or operating instruction protocols and cable 162 terminating in an interface 163. Interface 163 may communicate following connection to a mating interface provided on control console 100 or an intermediate interface component.

Figure 6:
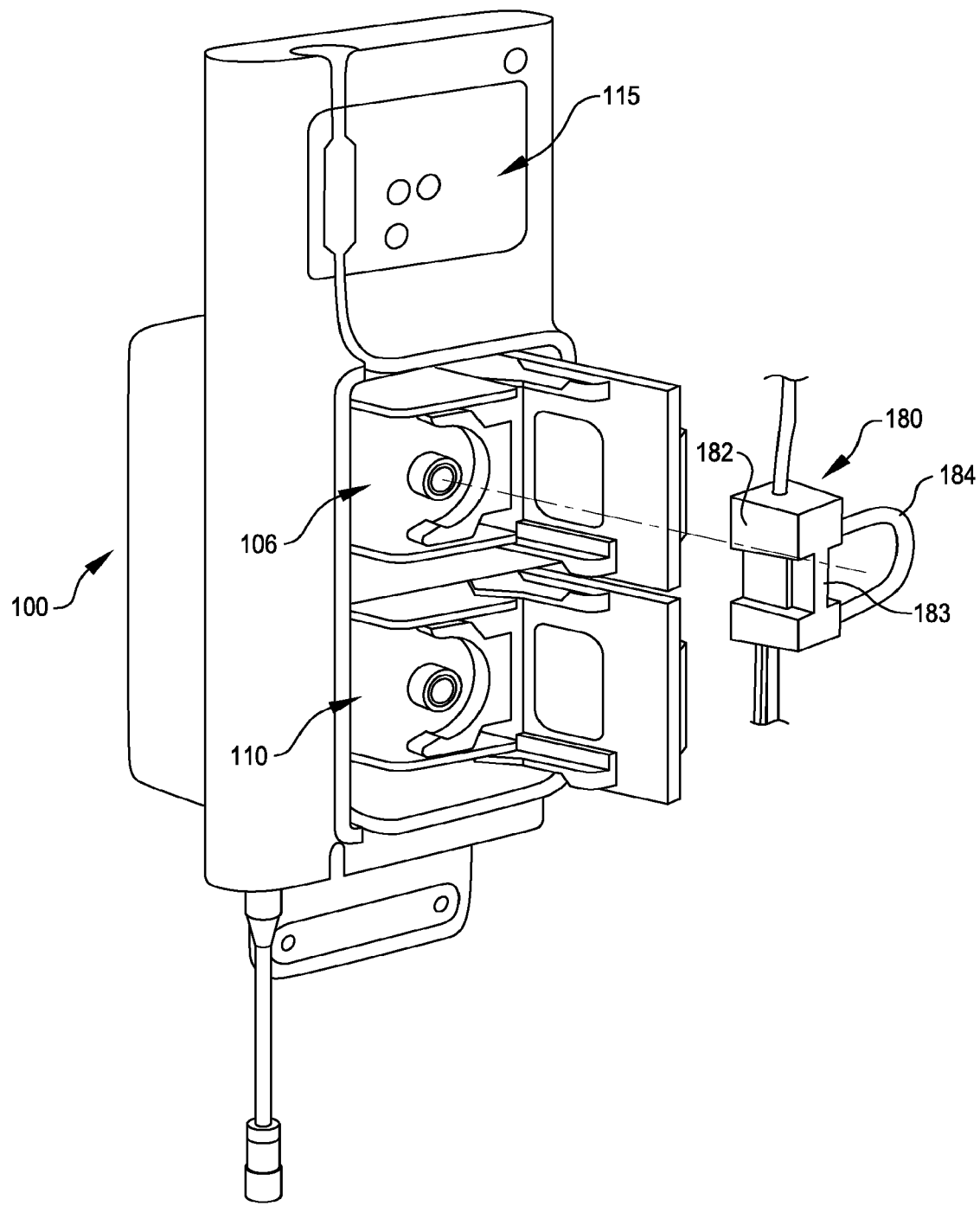
FIG. 6 shows a schematic view illustrating the interface of another adaptive tubing cassette with an aspiration or infusion system incorporated in a control console as illustrated in FIG. 1.

FIG. 6 illustrates an alternative embodiment of a preformed tubing cassette 180 according to the present invention comprising housing 182 having a centrally positioned handle 183 and a single preformed tubing loop 184. In alternative embodiments, tubing loop 184 may be sized and configured for mating with a tubing pathway formed as part of an infusion or aspiration system. This type of preformed tubing cassette having a single preformed tubing loop may be used, for example, with interventional catheter assemblies having either infusion or aspiration capabilities, but not both, and may otherwise interface with control console 100 similarly to the interface of adaptive tubing cassette 140, described above.

Figure 7A:
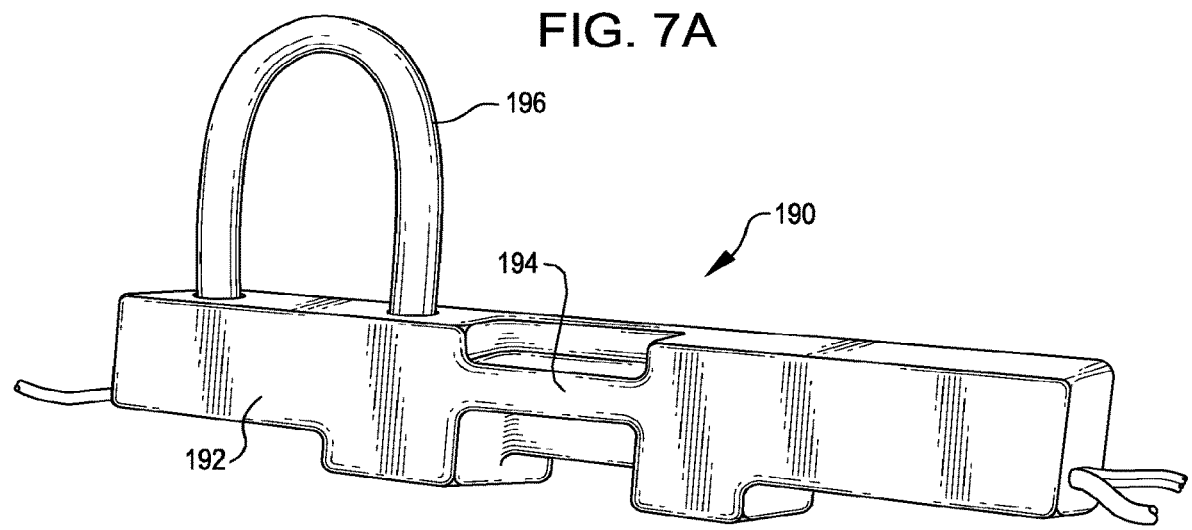
FIG. 7A shows a schematic view illustrating another embodiment of an adaptive tubing cassette suitable for use with an interventional catheter assembly having infusion capability.
Figure 7B:
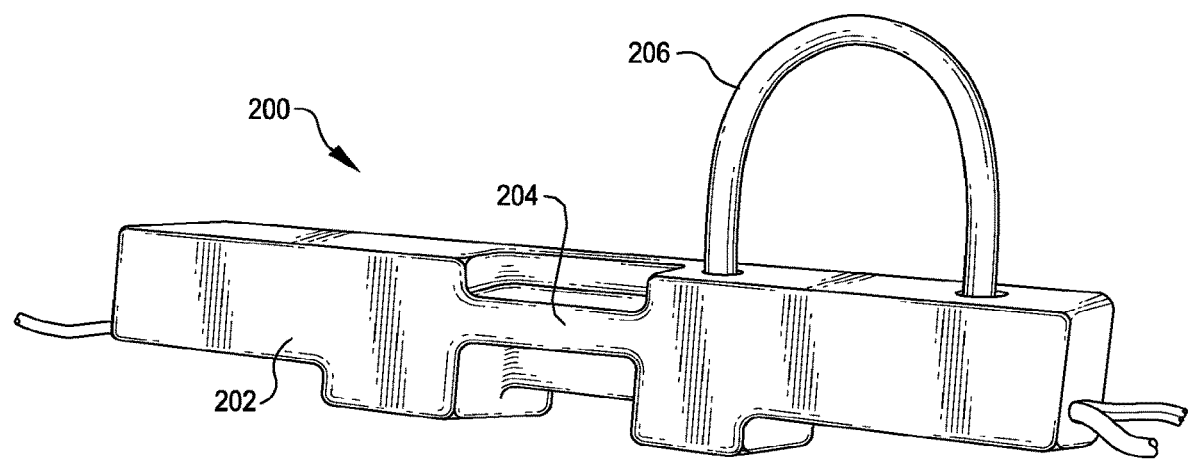
FIG. 7B shows a schematic view illustrating another embodiment of an adaptive tubing cassette suitable for use with an interventional catheter assembly having aspiration capability.

FIGS. 7A and 7B illustrate alternative embodiments of adaptive tubing cassettes 190 and 200, respectively, having housings 192 and 202, respectively, sized and configured for detachably mating with the control console in the area of the infusion and/or aspiration system(s). Adaptive tubing cassettes 190 and 200 have a central handle 194, 204 for grasping and incorporate preformed tubing loops 196, 206, respectively. Adaptive tubing cassette 190 is designed for use with an infusion (only) interventional catheter assembly; adaptive tubing cassette 200 is designed for use with an aspiration (only) interventional catheter assembly.

While the present invention has been described above with reference to the accompanying drawings in which particular embodiments are shown and explained, it is to be understood that persons skilled in the art may modify the embodiments described herein without departing from the spirit and broad scope of the invention. Accordingly, the descriptions provided above are considered as being illustrative and exemplary of specific structures, aspects and features within the broad scope of the present invention and not as limiting the scope of the invention.

We claim:

1. A medical system, comprising:
    a control console including a housing;
    a first peristaltic pump coupled to the housing;
    a second peristaltic pump coupled to the housing;
    a tubing cassette coupled to the housing;
    wherein the first peristaltic pump includes an infusion pathway designed to engage a first infusion tube of the tubing cassette;
    wherein the second peristaltic pump includes an aspiration pathway designed to engage a second aspiration tube of the tubing cassette;
    wherein the first infusion tube is different from the second aspiration tube;
    wherein the first infusion tube has a first wall thickness, and wherein the second aspiration tube has a second wall thickness different from the first wall thickness.

2. The medical system of claim 1, wherein the first peristaltic pump generates a first pressure within the first infusion tube, and wherein the second peristaltic pump generates a second pressure within the second aspiration tube, and wherein the first pressure is greater than the second pressure.

3. The medical system of claim 2, wherein the first peristaltic pump includes a first set of rollers designed to advance an infusion fluid through the first infusion tube at the first pressure.

4. The medical system of claim 3, wherein the second peristaltic pump includes a second set of rollers designed to advance an aspiration fluid through the second aspiration tube at the second pressure.

5. The medical system of claim 4, wherein the first pressure is less than or equal to 160 psi.

6. The medical system of claim 5, wherein the second pressure is less than or equal to 20 psi.

7. The medical system of claim 1, wherein the first infusion tube has a first stiffness, and wherein the second aspiration tube has a second stiffness different from the first stiffness.

8. The medical system of claim 1, wherein the first peristaltic pump, the second peristaltic pump or both the first peristaltic pump and the second peristaltic pump are positioned within the housing.

9. The medical system of claim 1, further comprising a control panel coupled to the housing.

10. The medical system of claim 1, wherein each of the first infusion tube and the second aspiration tube forms a U-shaped loop, and wherein each the first infusion tube and the second aspiration tube extends away from the tubing cassette in the same direction in a side-by-side arrangement.

11. A medical device system, comprising:
    a control console including an infusion system and an aspiration system;
    a tubing cassette including a first infusion tube and a second aspiration tube, wherein the first infusion tube is different from the second aspiration tube;
    wherein the infusion system includes an infusion pump defining an infusion pathway designed to mate with the first infusion tube;
    wherein the aspiration system includes an aspiration pump defining an aspiration pathway designed to mate with the second aspiration tube;
    wherein the infusion pump is designed to infuse fluid at a first pressure and wherein the aspiration pump is designed to aspirate fluid at a second pressure different from the first pressure;
    wherein the first infusion tube has a first stiffness, and wherein the second aspiration tube has a second stiffness different from the first stiffness.

12. The medical device system of claim 11, wherein the infusion pump includes a first set of rollers designed to infuse fluid through the first infusion tube at the first pressure, and wherein the aspiration pump includes a second set of rollers designed to advance an aspiration fluid through the second aspiration tube at the second pressure.

13. The medical device system of claim 11, wherein the first pressure is less than or equal to 160 psi.

14. The medical device system of claim 13, wherein the second pressure is less than or equal to 20 psi.

15. The medical device system of claim 11, wherein the first infusion tube has a first wall thickness, and wherein the second aspiration tube has a second wall thickness different from the first wall thickness.

16. The medical device system of claim 11, wherein the infusion pump, the aspiration pump or both the infusion pump and the aspiration pump are positioned within the control console.

17. The medical device system of claim 11, further comprising a control panel coupled to the control console.

18. A medical device system, comprising:
    a control console including a control panel, an infusion system and an aspiration system; and
    a tubing cassette including a high pressure tube and a low pressure tube extending away therefrom, wherein the high pressure tube is different from the low pressure tube;
    wherein the control panel is configured to communicate with the infusion system and the aspiration system;
    wherein the infusion system includes a high pressure tubing pathway including a first set of high pressure rollers;
    wherein the aspiration system includes a low pressure tubing pathway including a second set of low pressure rollers;
    wherein the first infusion tube has a first wall thickness and a first stiffness, and wherein the second aspiration tube has a second wall thickness and a second stiffness, and wherein the second wall thickness is different from the first wall thickness, the second stiffness is different from the first stiffness or both the second wall thickness is different from the first wall thickness and the second stiffness is different from the first stiffness.

* * * * *